United States Patent
Park et al.

(10) Patent No.: US 9,304,132 B2
(45) Date of Patent: Apr. 5, 2016

(54) MOLECULAR DELIVERY WITH NANOWIRES

(75) Inventors: Hongkun Park, Cambridge, MA (US); EunGyeong Yang, Seoul (KR); Alexander K. Shalek, Cambridge, MA (US); JinSeok Lee, Seoul (KR); Jacob Robinson, Somerville, MA (US); Amy Sutton, Cambridge, MA (US); Myung-Han Yoon, Gwangju (KR); Marsela Jorgolli, Arlington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/264,587

(22) PCT Filed: Apr. 16, 2010

(86) PCT No.: PCT/US2010/031392
§ 371 (c)(1),
(2), (4) Date: Dec. 8, 2011

(87) PCT Pub. No.: WO2010/121130
PCT Pub. Date: Oct. 21, 2010

(65) Prior Publication Data
US 2012/0094382 A1  Apr. 19, 2012

Related U.S. Application Data

(60) Provisional application No. 61/169,837, filed on Apr. 16, 2009.

(51) Int. Cl.
| | |
|---|---|
| *C12M 1/00* | (2006.01) |
| *C12Q 1/68* | (2006.01) |
| *G01N 33/567* | (2006.01) |
| *C12M 1/34* | (2006.01) |
| *C12N 15/00* | (2006.01) |
| *C12N 15/74* | (2006.01) |
| *C07H 21/02* | (2006.01) |
| *G01N 31/22* | (2006.01) |
| *G01N 33/543* | (2006.01) |
| *G01N 33/50* | (2006.01) |

(52) U.S. Cl.
CPC ...... *G01N 33/54353* (2013.01); *G01N 33/5008* (2013.01)

(58) Field of Classification Search
CPC .............. G01N 33/5008; G01N 33/54353; B01J 2219/00497
USPC ........... 435/6.1, 7.21, 283.1, 287.2, 455, 471; 536/23.1; 422/430; 977/762, 902
See application file for complete search history.

(56) References Cited

U.S. PATENT DOCUMENTS

| | | | |
|---|---|---|---|
| 5,381,753 A | 1/1995 | Okajima et al. | |
| 5,688,642 A * | 11/1997 | Chrisey et al. | ............... 435/6.11 |
| 5,858,862 A | 1/1999 | Westwater et al. | |
| 6,123,819 A | 9/2000 | Peeters | |
| 6,286,226 B1 | 9/2001 | Jin | |
| 7,163,659 B2 * | 1/2007 | Stasiak et al. | ............... 422/82.01 |
| 7,795,039 B2 | 9/2010 | Spira et al. | |
| 2003/0027327 A1 | 2/2003 | Cunningham et al. | |
| 2004/0106203 A1 | 6/2004 | Stasiak et al. | |
| 2004/0182707 A1 | 9/2004 | Jardemark et al. | |
| 2005/0221072 A1 | 10/2005 | Dubrow et al. | |
| 2006/0214156 A1 | 9/2006 | Pan et al. | |
| 2007/0187840 A1 | 8/2007 | Dell'acqua-bellavitis et al. | |
| 2008/0248575 A1 | 10/2008 | Lee et al. | |
| 2009/0312194 A1 | 12/2009 | Tyner et al. | |
| 2010/0038247 A1 | 2/2010 | Zimmermann et al. | |
| 2010/0140111 A1 | 6/2010 | Gimsa et al. | |
| 2010/0213579 A1 | 8/2010 | Henry et al. | |
| 2010/0233226 A1 | 9/2010 | Ferain et al. | |
| 2011/0006674 A1 | 1/2011 | Naaman et al. | |
| 2011/0104732 A1 | 5/2011 | Lucic et al. | |
| 2011/0291643 A1 | 12/2011 | Ravindran et al. | |
| 2011/0309237 A1 | 12/2011 | Seo et al. | |
| 2013/0260467 A1 | 10/2013 | Park et al. | |
| 2013/0284612 A1 | 10/2013 | Park et al. | |
| 2015/0191688 A1 | 7/2015 | Park et al. | |
| 2015/0197807 A1 | 7/2015 | Park et al. | |
| 2015/0203348 A1 | 7/2015 | Park et al. | |

FOREIGN PATENT DOCUMENTS

| | | |
|---|---|---|
| EP | 2 447 354 A1 | 5/2012 |
| JP | 2001-153738 A | 6/2001 |
| JP | 2004-184414 A | 7/2004 |

(Continued)

OTHER PUBLICATIONS

Park et al. Selective surface functionalization of silicon nanowires via nanoscale joule heating. Nano Letters. 2007;7(10):3106-3111.*
Park et al, Selective Surface Functionalization of Silicon Nanowires via Nanoscale Joule Heating, 2007, Nano Letters, 7, Supporting information, pp. 1-7.*
Berthing, T., et al. "Applications of nanowire arrays in nanomedicine" *Journal of Nanoneuroscienc* vol. 1, No. 1 (2009) pp. 3-9.
Woong Kim, et al. "Interfacing Silicon Nanowires with Mammalian Cells" *Journal of the American Chemical Society*, vol. 129, No. 23 (Jun. 1, 2007) pp. 7228-7229.
Hughes, et al. "Nanostructure-mediated drug delivery" *Nanomedicine: Nanotechnology Biology and Medicine*, vol. 1, No. 1 (Mar. 1, 2005) pp. 22-30.

(Continued)

*Primary Examiner* — Narayan Bhat
(74) *Attorney, Agent, or Firm* — Wolf, Greenfield & Sacks, P.C.

(57) ABSTRACT

A molecular delivery system including a plurality of nanowires (e.g., Si NWs), each of the nanowires having a surface layer formed of a silicon-containing material and a covalently bound linker (e.g., silane linker) attached to the surface layer, and optionally including a substrate to which the nanowires are adhered or a molecule to be delivered attached to the linker. Also disclosed is a method of delivering into a cell an exogenous molecule.

18 Claims, 2 Drawing Sheets

(56) References Cited

FOREIGN PATENT DOCUMENTS

| JP | 2007-519405 | A | | 7/2007 |
|----|----|----|----|----|
| JP | 2011-500184 | A | | 1/2011 |
| JP | 2012-501642 | A | | 1/2012 |
| SG | WO 2008/018834 | | * | 2/2008 |
| WO | 2004/036202 | | | 4/2004 |
| WO | WO 2005/075656 | A1 | | 8/2005 |
| WO | 2005/093831 | | | 10/2005 |
| WO | 2009/050168 | | | 4/2009 |
| WO | 2009/104056 | | | 8/2009 |
| WO | 2010/003062 | | | 1/2010 |
| WO | WO 2010/003062 | A2 | | 1/2010 |
| WO | WO 2010/026450 | A1 | | 3/2010 |
| WO | WO 2010/121130 | A2 | | 10/2010 |
| WO | WO 2012/050876 | A2 | | 4/2012 |
| WO | WO 2012/050881 | A2 | | 4/2012 |
| WO | WO 2014/031171 | A1 | | 2/2014 |
| WO | WO 2014/031172 | A1 | | 2/2014 |

OTHER PUBLICATIONS

International Search Report and Written Opinion for Application No. PCT/US2010/031392 mailed Aug. 16, 2011.
International Preliminary Report on Patentability for Application No. PCT/US2010/031392 mailed Oct. 27, 2011.
International Search Report and Written Opinion for Application No. PCT/US2011/053640 mailed Sep. 25, 2012.
International Preliminary Report on Patentability for Application No. PCT/US2011/053640 mailed Apr. 11, 2013.
International Search Report and Written Opinion for Application No. PCT/US2011/053646 mailed Jul. 11, 2012.
International Preliminary Report on Patentability for Application No. PCT/US2011/053646 mailed Apr. 2, 2013.
International Search Report and Written Opinion for Application No. PCT/US2013/032457 mailed Jun. 10, 2013.
International Search Report and Written Opinion for Application No. PCT/US2013/032486 mailed Sep. 17, 2013.
International Search Report and Written Opinion for Application No. PCT/US2013/032512 mailed Aug. 1, 2013.
[No Author Listed] Neon™ Transfection System Product Information at <http://www.lifetechnologies.com/us/en/home/life-science/cell-culture/transfection/transfection---selection-misc/neon-transfection-system/neon-transfection-system-information.html> 2013. Life Technologies Corporation.
[No Author Listed] Nuclearfector™ Kits for Rat Neurons at <http://www.lonza.com/products-services/bio-research/transfection/nucleofector-kits-for-primary-cells/nucleofector-kits-for-primary-neural-cells/nucleofector-kits-for-rat-neurons.aspx> Last accessed Sep. 30, 2013. Lonza Group Ltd.
Agarwal et al., Effect of cell size and shape on single-cell electroporation. Anal Chem. May 15, 2007;79(10):3589-96. Epub Apr. 20, 2007.
Chang et al., Changes in membrane structure induced by electroporation as revealed by rapid-freezing electron microscopy. Biophysical Journal. Jul. 1990;58(1):1-12.
Chuang et al, Inhibition of CD36-dependent phagocytosis by prostaglandin E2 contributes to the development of endometriosis. Am J Pathol. Feb. 2010;176(2):850-60. Epub Dec. 24, 2009.
Gersten et al., Electromagnetic theory of enhanced Raman scattering by molecules adsorbed on rough surfaces. J Chem Phys. Oct. 1, 1980;73(7):3023-37.
Hochbaum et al., Controlled growth of Si nanowire arrays for device integration. Nano Lett. Mar. 2005;5(3):457-60.
Lee et al., Layer-by-layer assembly of zeolite crystals on glass with polyelectrolytes as ionic linkers. J Am Chem Soc. Oct. 10, 2001;123(40):9769-79.

Lee et al., Vapor-liquid-solid and vapor-solid growth of phase-change Sb2Te3 nanowires and Sb2Te3/GeTe nanowire heterostructures. J Am Chem Soc. May 14, 2008;130(19):6252-8. Epub Apr. 11, 2008.
Martensson et al., Epitaxial III-V Nanowires on Silicon. Nano Letters. Sep. 2004;4(10):1987-90.
Meister et al., Mechanisms of gene silencing by double-stranded RNA. Nature. Sep. 16, 2004;431(7006):343-9.
Okita et al., Generation of mouse induced pluripotent stem cells without viral vectors. Science. Nov. 7, 2008;322(5903):949-53. Epub Oct. 9, 2008.
Olofsson et al., Single-cell electroporation. Curr Opin Biotechnol. Feb. 2003;14(1):29-34.
Park, Vertical Nanowire Platform: Leveraging Semiconductor Technology to Develop Biological Tools. Seminar at Stanford. May 2012. Abstract.
Raffa et al., Carbon nanotube-enhanced cell electropermeabilisation. Bioelectrochemistry. Aug. 2010;79(1):136-41. Epub Nov. 2, 2009.
Shalek et al., Chemical and electrical interrogation of biological networks using vertical nanowires. Pioneer Awards, NIH. Sep. 2011. Poster.
Shalek et al., Nanowire-mediated delivery enables functional interrogation of primary immune cells: application to the analysis of chronic lymphocytic leukemia. Nano Lett. Dec. 12, 2012;12(12):6498-504. Epub Dec. 3, 2012.
Shalek et al., Nanowire-mediated delivery enables functional interrogation of primary immune cells: application to the analysis of chronic lymphocytic leukemia. Nano Lett. Dec. 12, 2012;12(12):6498-504. Epub 2012 Dec. 3, Supporting Information. 43 pages.
Shalek et al., Vertical silicon nanowires as a universal platform for delivering biomolecules into living cells. Proc Natl Acad Sci U S A. Feb. 2, 2010;107(5):1870-5. Epub Jan. 11, 2010.
Van Tendeloo et al., Highly efficient gene delivery by mRNA electroporation in human hematopoietic cells: superiority to lipofection and passive pulsing of mRNA and to electroporation of plasmid cDNA for tumor antigen loading of dendritic cells. Blood. Jul. 1, 2001;98(1):49-56.
Vierbuchen et al., Direct conversion of fibroblasts to functional neurons by defined factors. Nature. Feb. 25, 2010;463(7284):1035-41. Epub Jan. 27, 2010.
Wang et al., Sensitivity to Wnt pathway inhibition in CLL is associated with specific gene espression signatures. Blood (ASH Annual Meeting Abstracts) Nov. 2011;118(21):364. Abstract.
Wokaun et al., Radiation damping in surface-enhanced Raman scattering. Phys Rev Lett. Apr. 5, 1982;48:957-60.
Xia et al., siRNA-mediated gene silencing in vitro and in vivo. Nat Biotechnol. Oct. 2002;20(10):1006-10. Epub Sep. 16, 2002.
Xu et al., Dependence of axon initial segment formation on Na+ channel expression. J Neurosci Res. Feb. 15, 2005;79(4):428-41.
Zhao et al., High-efficiency transfection of primary human and mouse T lymphocytes using RNA electroporation. Mol Ther. Jan. 2006;13(1):151-9. Epub Sep. 2, 2005.
Chinese Office Action mailed May 23, 2014 for Application No. 201180051218.4.
Restriction Requirement for U.S. Appl. No. 13/876,066 mailed Dec. 11, 2013.
Office Action for U.S. Appl. No. 13/876,066 mailed Apr. 16, 2014.
Tsakalakos et al., Strong broadband optical absorption in silicon nanowire films. Journal of Nanophotonics. Jul. 17, 2007; 1:013552.
Singapore Search Report and Written Opinion dated Jun. 30, 2014 for Application No. SG 201302254-6.
Held et al. Microneedle arrays for intracellular recording applications. Micro Electro Mechanical Systems. MEMS 2008. IEEE 21s International Conference; Jan. 17, 2008; 13-17:268-271.

(56) References Cited

OTHER PUBLICATIONS

Chinese Office Action mailed Oct. 30, 2014 for Application No. 201180051218.4.
Final Office Action dated Dec. 5, 2014 for U.S. Appl. No. 13/876,066.
Peng et al., Dendrite-assisted growth of silicon nanowires in electroless metal deposition. Adv Funct Mater. 2003; 13:127-132.
Peng et al., Fabrication of large-area silicon nanowire p-n junction diode arrays. Adv Mater. 2004; 16:73-76.
Chinese Office Action mailed Feb. 9, 2015 for Application No. 201180051218.4.
Singapore Examination Report dated Feb. 27, 2015 for Application No. 201302254-6.
International Preliminary Report on Patentability for Application No. PCT/US2013/032457 mailed Mar. 5, 2015.
International Preliminary Report on Patentability for Application No. PCT/US2013/032486 mailed Mar. 5, 2015.
International Preliminary Report on Patentability for Application No. PCT/US2013/032512 mailed Mar. 5, 2015.
European Office Action mailed Jul. 3, 2015 for Application No. 11770260.5.
Japanese Office Action mailed Jun. 23, 2015 for Application No. 2013-531762.
Office Action for U.S. Appl. No. 13/876,066 mailed Jul. 8, 2015.
Hwang et al., High density n—Si/n—TiO2 core/shell nanowire arrays with enhanced photoactivity. Nano Lett. Jan. 2009;9(1):410-5. doi: 10.1021/n18032763.

* cited by examiner

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
gauccugcug gccgagcuct t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
ggcacgucuu gaccuugaat t                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
gaagaauggu acaaauccat t                                              21

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 4
ucgacccuga cgccacutt                                                 19

<210> SEQ ID NO 5
<211> LENGTH: 19
<212> TYPE: DNA
```

-continued

```
<213> ORGANISM: Artificial Sequence
<220> FEATURE:
<223> OTHER INFORMATION: Synthetic oligonucleotide

<400> SEQUENCE: 5
acugagaacu aagagagtt                                                    19
```

MOLECULAR DELIVERY WITH NANOWIRES

CROSS REFERENCE TO RELATED APPLICATIONS

This application claims priority of PCT Application PCT/US2010/031392, filed on Apr. 16, 2010, which claims priority of U.S. Provisional Application 61/169,837, filed on Apr. 16, 2009. These prior applications are incorporated herein by reference in their entirety.

STATEMENT AS TO FEDERALLY SPONSORED RESEARCH

This invention was made with government support under contract number 1DP1OD003893-01 awarded by the National Institutes of Health. The government has certain rights in the invention.

BACKGROUND

It is of great interest to control cellular functions by delivering exogenous species into cells. Traditionally, this task is accomplished by delivering genes into a cell so that the genetic information is transcribed to RNAs and then translated into proteins that regulate specific cell functions.

Currently, delivery of exogenous genetic materials into cells can be achieved by numerous approaches, including viral (e.g., adeno-associated and lenti-viral vectors, and Bac-Mam), physio-chemical (e.g., calcium phosphate, electroporation, liposome, and polycation-mediated), and mechanical methods (e.g., microinjection).

A high-throughput method is yet to be developed for delivering exogenous materials in general (including non-genetic materials) into cells of different types. Indeed, there is a demand for a method that is not only efficient and scalable, but also allows for localized delivery at different positions within a cell and massively parallel analysis of the impacts of different chemical and biological species on cellular functions.

SUMMARY

This invention is based on the unexpected discovery that certain nanometer scale materials ("nanomaterials") have high efficiency in delivering an exogenous molecule (e.g., a nucleic acid, a protein, a polysaccharide, or a small molecule) into a cell. Thus, this invention relates to a nanomaterials-based delivery system and its use.

In one aspect, this invention features a molecular delivery system including a substrate, and a plurality of nanowires attached to a surface of the substrate. Each of the nanowires has a surface layer formed of a silicon-containing material and a silane linker attached to the surface layer. The term "nanowire" (or "NW") refers to a material in the shape of a wire or rod having a diameter in the range of 1 nm to 1 µm. The term "silane linker" refers to a compound having a silyl functional group at one end and another functional group (such as amino) at the other.

This system may include one or more of the following features.

The system may further include a first molecule to be delivered (e.g., a small molecule, a nucleic acid, a protein, or a polysaccharide), either attached to the linker permanently (i.e., not detachable from the linker in a cell) or reversibly (i.e., detachable from the linker in a cell). The system may further include a second molecule to be delivered (e.g., a small molecule, a nucleic acid, a protein, or a polysaccharide), either attached to the linker permanently or reversibly. The first and second molecules are different molecules. They may be connected to the same NW or different NWs. NWs on the same substrate may have different silane linkers for delivering different molecules. The majority of the NWs attached to the surface may extend along a uniform direction, such as a substantially vertical direction (i.e., 60-90 degree) to the substrate surface. The NWs can have a length of 20 nm to 10 µm (e.g., 50 nm-5 µm), a diameter of 1-500 nm (e.g., 1-250 nm), or a density of 0.001-10 wires/µm$^2$. The silicon-containing material in the surface layer of each NW can be elemental silicon, silicon oxide, silicon nitride, or silicon carbide. The silane linker can be propylaminosilane.

The term "small molecule" refers to any molecule with a molecular weight (or "MW") below 1000 Da, including various drug molecules, oligosaccharides, oligonucleotides, and peptides. On the other hand, the terms "nucleic acid," "protein," and "polysaccharide" all refers to larger molecules, i.e., having a MW of at least 1000 Da.

In another aspect, this invention relates to a method of delivering an exogenous molecule into a cell (such as stem cells, immune cells, and primary cells). The method includes providing a substrate having a surface and a plurality of nanowires (preferably inorganic nanowires) adhered to the surface, in which each of the nanowires has a covalently bound linker to which a molecule to be delivered is attached; and contacting the nanowires with a cell to allow penetration of the nanowires into the cell, whereby the molecule is delivered into the cell.

This method may include one or more of the following features. Each of the nanowires may have a surface layer formed of a silicon-containing material and the linker is covalently bound to the surface layer. The nanowires can be adhered to the surface along a substantially vertical direction to the surface. The molecule to be delivered may be attached to the linker reversibly. The molecule to be delivered can be a nucleic acid (e.g., DNA, including linear and plasmid DNAs; and RNA, including mRNA, siRNA and microRNA), a protein, a polysaccharide, or a small molecule. The molecules connected to different NWs may be different so as to allow site-specific delivery. The linker can be a silane linker (e.g., propylaminosilane).

Still another aspect of the invention relates to a molecular delivery system that includes a plurality of silicon nanowires, wherein each nanowire has a covalently bound linker (e.g., a silane linker) to which a molecule is attached.

Also within the scope of this invention is a method for molecular delivery using the system immediately described above.

The system and method immediately described above may include one or more of the following features. The silicon nanowires may be free standing or attached to a substrate. The molecule to be delivered may be attached to the linker reversibly. The molecule to be delivered can be a nucleic acid (e.g., DNA and RNA including siRNA and microRNA), a protein, a polysaccharide, or a small molecule. The linker can be a silane linker (e.g., propylaminosilane or mercaptosilanes).

The systems described above can be used for delivering various molecules both in vitro and in vivo.

One advantage of the above-described delivery systems and methods is that exogenous molecules (e.g., RNAs, peptides, and proteins) can be delivered into cells with unexpectedly high efficiency. As a result, unwanted side effects associated with gene transfection or transduction (such as introducing cancerous genes into the genome or activating multiple different subcellular pathways) are greatly decreased. Also, given the high delivery efficiency, massive parallel screening (i.e., assaying different molecules in the same cell or different cells in a short period of time) can be achieved. For example, one can use the delivery system in proteomics by attaching one type of protein antibodies to NWs contained in one address of the substrate and then screening for proteins in a specific cell type.

In addition, NWs can be used to deliver molecules to almost all of the eukaryotic and prokaryotic cells by varying their geometry (e.g., size). Transitioning to prokaryotic cells would enable a wealth of new applications including large-scale parallel antibiotic screening. NWs on silicon wafers can easily be mass produced by any semiconductor foundry. This high-throughput, low-cost production allows wide-range application of the delivery methods of this invention.

The details of one or more embodiments are set forth in the accompanying description below. Other aspects, features, and advantages will be apparent from the following drawing, detailed description of embodiments, and also from the appending claims.

DETAILED DESCRIPTION

Figure 1:
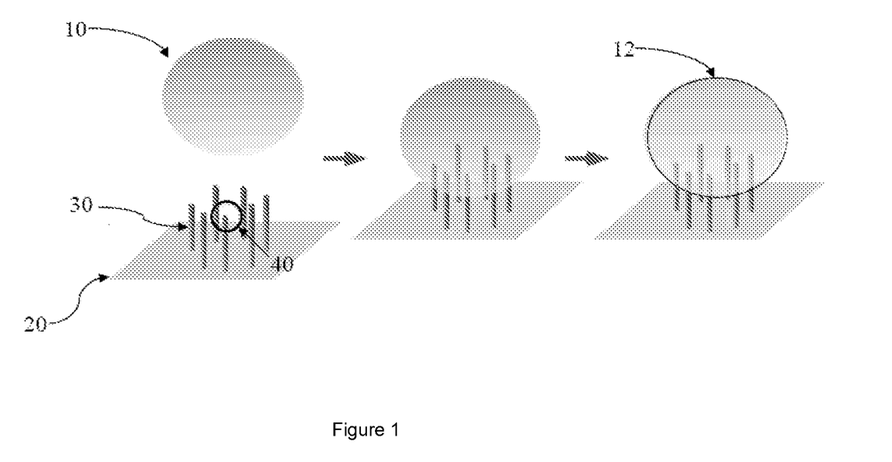
FIG. 1 is a schematic of a molecular delivery process using an embodiment of the invention.
Figure 2:
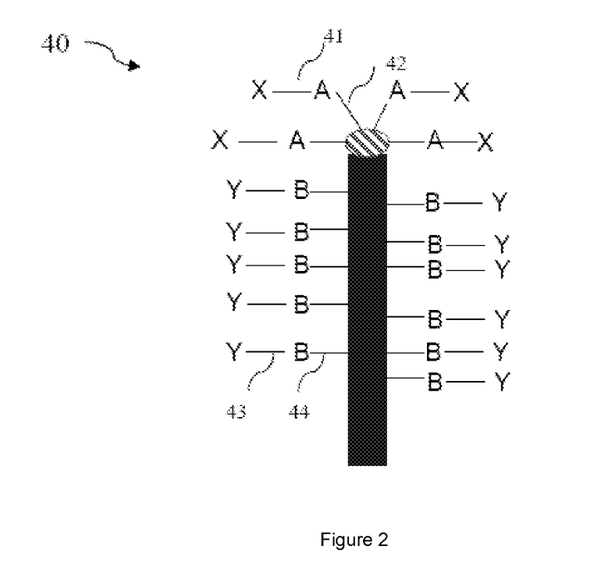
FIG. 2 is an enlarged schematic of circled area 40 of the delivery system in FIG. 1.

This invention relates to a NW-based molecular delivery system and a method of using the system to deliver exogenous molecules into cells. Referring to FIG. 1, a cell 10 is brought into contact with a substrate 20 having an array of vertical NWs 30. The NWs, as illustrated in FIG. 2, have molecules to be delivered X and Y attached to the NW surface through linker A and B respectively. Penetration of surface-modified NWs 30 into cell 10 results in delivering the molecules X and Y into the cell. The introduction of molecules X and Y into the cytoplasm may impact cellular function of cell 10, as illustrated by hypothetical circle 12 around cell 10.

NWs used in this invention can be formed of material with low cytoxicity, such as silicon, silicon oxide, silicon nitride, silicon carbide, iron oxide, aluminum oxide, iridium oxide, tungsten, stainless steel, silver, platinum, and gold. Preferably, the NWs are grown on a substrate to allow site-specific delivery of molecules of interest into cells. This site-specific delivery can be achieved by patterning molecules or the NWs via, e.g., microarraying, stamping, applying masks, ink jet printing, or hand-printing, or by controlling cell plating site. The site-specific delivery, in turn, not only allows simultaneous assaying of the effects of different molecules delivered into cells, but also allows for testing of the interactions between cells to which different molecules have been introduced.

Two approaches are widely used for obtaining an array of NWs on a substrate. One is the so-called bottom-up approach, which essentially involves growing NWs from a precursor material. Taking chemical vapor deposition (CVD) for example, the NW growth process begins by placing or patterning catalyst or seed particles (usually with a diameter of 1 nm to a few hundred nanometers) atop a substrate; next, a precursor material is added to the catalyst or seed particles; and when the particles become saturated with the precursor, NWs begin to grow in a shape that minimizes the system's energy. By varying the precursor, substrate, catalyst/seed particles (e.g., size, density and deposition method on the substrate), and growth conditions, NWs can be made in a variety of materials, sizes, and shapes, at sites of choice. Another approach, the top-down process, essentially involves removing (e.g., by etching) predefined structures from a supporting substrate. For instance, the sites where the NWs are to be formed are first patterned into a soft mask (e.g., photoresist), which is either used to protect the sites that NWs will be formed during a subsequent etch or to pattern a hard mask; an etching step is subsequently performed (either wet or dry) to develop the patterned sites into three-dimensional wires.

Molecular delivery efficiency to different cell types can be manipulated by varying the NW size or density. For example, silicon NWs with a diameter of less than 200 nm, a length of 2.5-5 $\mu m$, and a density of 0.5-5/$\mu m^2$ show unexpectedly high delivery efficiency to neurons while silicon NWs with a diameter of less than 200 nm, a length of 0.5-2.5 $\mu m$, and a density of 0.01-10/$\mu m^2$ show unexpectedly high delivery efficiency to human fibroblasts.

NWs used in the invention can also be free standing wires, (i.e., not bound to a substrate). Free standing NWs can be synthesized by methods well known in the field, such as sol-gel reactions with a porous template and solution reactions with surfactants.

The thus-made NWs described above then undergo surface modification so that various molecules of interest can be attached to them. Referring back to FIG. 2, a modified NW may have a tip (shown as an oval filled with slant lines) and an elongated body (shown as a solid rectangle). The tip may be a catalyst particle if the NW is produced by the bottom-up approach or a mask particle if the NW is produced by the top-down approach. Alternatively, the NW may not have a tip.

The tip, if present, is coated with one or more molecule X's connected to the tip via linker A. The NW body is coated with one or more molecule Y's connected to the tip via linker B.

With different surface modification materials or methods, the interaction between the linker A (or B) and the NW, labeled as 42 (or 44) can be covalent, electrostatic, photosensitive, or hydrolysable (e.g., with or without an enzyme). For example, a silane (or thiol) compound can be applied to a NW with a surface layer of an oxide such as silicon oxide (or Au). As a result, the interaction 42 (or 44) is covalent, such as an O—Si or Au—S bond. Examples of the silane compound for surface modification include, but are not limited to, aminosilanes such as (3-aminopropyl)-trimethoxysilane, (3-aminopropyl)-triethoxysilane, 3-(2-aminoethylamino)propyl-dimethoxymethylsilane, (3-aminopropyl)-diethoxymethylsilane, [3-(2-aminoethylamino)propyl]trimethoxysilane, bis[3-(trimethoxysilyl)propyl]amine, and (11-aminoundecyl)-triethoxysilane; glycidoxysilanes such as 3-glycidoxypropyldimethylethoxysilane and 3-glycidyloxypropyl)trimethoxysilane; mercaptosilanes such as (3-mercaptopropyl)-trimethoxysilane and (11-mercaptoundecyl)-trimethoxysilane; and other silanes such as trimethoxy(octyl)silane, trichloro(propyl)silane, trimethoxyphenylsilane, trimethoxy(2-phenylethyl)silane, allyltriethoxysilane, allyltrimethoxysilane, 3-[bis(2-hydroxyethyl)amino]propyl-triethoxysilane, 3-cyanopropyltriethoxysilane, triethoxy(3-isocyanatopropyl)silane, 3-(trichlorosilyl)propyl methacrylate, and (3-bromopropyl)trimethoxysilane.

Other chemicals can be used to form linker A (or B). For example, any compound that attachable to silica such as polylysine, collagen, fibronectin, laminin, can be applied to a NW with a surface layer formed of silicon oxide.

Similarly, the interaction between the molecule X (or Y) and linker A (or B), labeled as 41 (or 43), can also selected to be covalent, electrostatic, photosensitive, or hydrolysable. In one embodiment, the interaction 41 (or 43) is electrostatic, such that X (or Y) can be detached from the NW and released into the cytoplasm. In an example, linker A is an aminosilane which carries positive charges due to the amino group and X is a nucleic acid which carries negative charges. In another embodiment, the interaction 41 (or 43) is covalent, such that X (or Y) can be removed from the cytoplasm by disconnecting the cell with the NW.

In a preferred embodiment, silicon NWs with a native oxide layer is treated with propylaminotrimethoxysilane for molecular delivery with high efficiency (~90-100%). Other silane linkers that exhibit high deliver efficiency include 11-aminoundecyl)-triethoxysilane, (3-mercaptopropyl)-trimethoxysilane, and (11-mercaptoundecyl)-trimethoxysilane.

After the molecule to be delivered is attached to NWs, cells can be plated on the NW substrate in a manner similar to plating them on a normal glass cover slip. The cells impale themselves, typically within an hour. Afterwards, the molecule may be released, e.g., by simply detaching from the NWs if it is electrostatically attached to the NWs. The effects of the molecule on the cells can then be examined. Unexpectedly, the cells (including both primary and cell lines) penetrated by NWs can survive, divide, and function for more than a week.

Other contemplated uses of the delivery systems described above include:

Designer cell networks: Research models that involve interacting cells and perturbations thereto can be designed and studied. Cellular systems normally difficult to achieve, such as synaptic pairs of neurons with different perturbations, can be constructed to model diseases (e.g., neurodegenerative diseases such as Alzheimer's), helping in the search for cures.

Gene-free reprogramming of differentiated cells into induced pluripotent stem cells: Reprogramming can be induced by delivering proteins or RNAs to a set of cells.

Assays of epigenetic factors: The delivery systems can be used to study the effects of numerous molecules on differentiating or altering the development of any set of cells, such as stem cells, induced pluripotent stem cells, and already differentiated tissues. Once the chemicals to develop a particular cell linage are discovered, the delivery system can be used to generate that line.

Dose-response assays: The delivery system can be used to study the concentration-dependent effects of a particular protein, RNA, drug, and/or combinations thereof.

Cellular pathway screening: By perturbing different elements of a particular cellular pathway, the causal relationships between those elements can be discovered.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

NW Array Fabrication

An array of Si NWs on a silicon substrate was formed by etching a silicon wafer covered with a 200 nm thick thermally-gown silicon oxide layer. First, colloidal gold nanoparticles (average diameter 100 nm, purchased from Ted Pella, used after concentrated the purchased sample by about 17 times) were suspended in a solution of 3% polymethyl-methacrylate (PMMA) in chlorobenzene to form a suspension. The silicon wafer was then spun coated at 3000 RPM with the suspension to produce a 100 nm thick PMMA-nanoparticle film on the wafer's surface. The wafer was then treated with a $CF_4$ plasma in a reactive ion etching (RIE) system (NEXX SYSTEMS CIRRUS 150) for 3 minutes to etch the silicon oxide in the regions that were not directly under the gold nanoparticles. The gold nanoparticles were then etched away with a TFA gold etchant to generate a pattern of disconnected silicon oxide dots. The pattern, covering the silicon wafer, acted as a mask for etching the wafer to form vertical NWs. The wafer was etched with an inductively-coupled $HBr:O_2$ plasma for 10 minutes in another RIE system (SURFACE TECHNOLOGY SYSTEMS ICP RIE) to afford an array of Si NWs (average length: 1000 nm; average diameter: 150 nm; density: 0.5 wire/$\mu m^2$). Lastly, the silicon oxide mask was removed by dipping the wafer in 49% hydrofluoric acid.

Example 2

Plating Cells on a NW Array

Confluent human fibroblasts, previously differentiated from embryonic stem cells, were removed from culture flasks by a five minute trypsin treatment. After quenching the enzyme with culture media, the cells were re-suspended to a concentration of 1 million cells/mL. Next, 10 uL of the cell suspension was plated atop the Si—NWs array sample of Example 1 and they were placed in the incubator (5% $CO_2$, 90% relative humidity). After 15 minutes of incubator, 700 uL of additional media was added.

Figure 3:
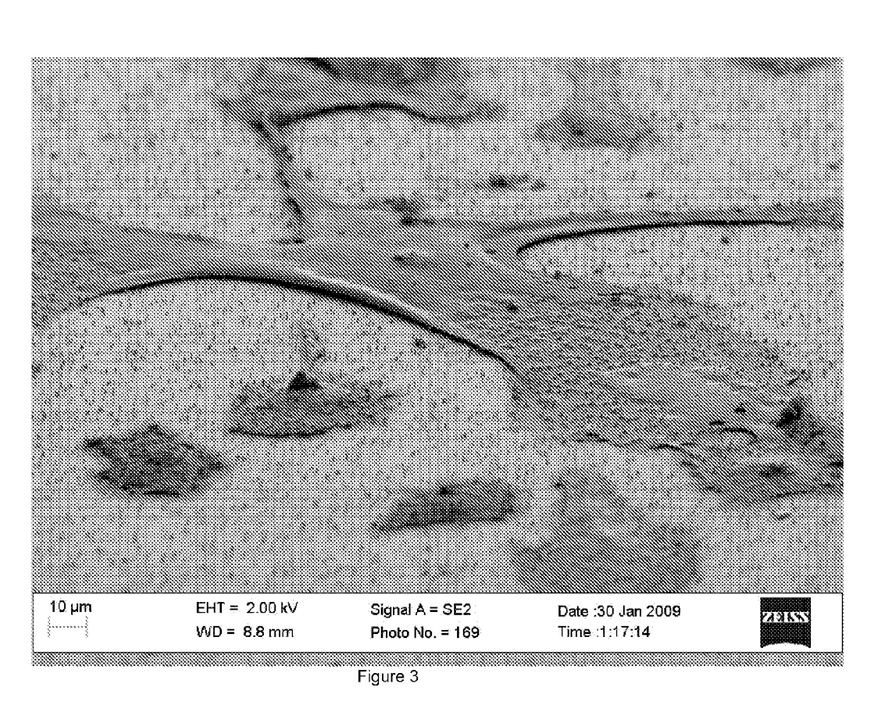
FIG. 3 is a scanning electron micrograph of human fibroblasts plated on a silicon chip having a silicon NW array.

One day later, the human fibroblasts were fixed in a solution of 4% gluteraldehyde in 0.1 M sodium cacodylate for 2 hours. They were then rinsed through 0.1 M sodium cacodylate. Next, a second fixation step was performed in a solution of 1% osmium tetroxide in 0.1 M sodium cacodylate for 2 hours. The cells were again rinsed through 0.1 M sodium cacodylate and then dehydrated in gradually increasing concentrations of ethanol from 50-100% in water. After dehydration in ethanol the samples were dried in a critical point dryer and then sputtered coated with a few nanometers of Pt/Pd before SEM imaging. As demonstrated by the SEM image of FIG. 3, the cells were penetrated by a number of NWs of the array.

Example 3

Peptide Delivery

Silicon substrates with vertically etched Si NWs prepared in Example 1 were rinsed with isopropanol three times and dried under nitrogen. The Si NW substrates were then incubated with 3-aminopropyltrimethoxysilane in toluene at 1% (v/v) in a nitrogen atmosphere at room temperature for 1 hr. The silanized Si NW substrates were sequentially washed with excess toluene three times and placed in a tris-buffered saline solution for 1 hour. Next, they were rinsed in 70% ethanol three times and placed into a biosafety cabinet in 70% ethanol. After 30 minutes, they were rinsed in DI water three times and dried under nitrogen. 5 μL solution of a short rhodamine-labeled peptide (concentration ~1 μg/μL) was then deposited on the surface of silanized substrates so that the peptide was electrostatically bound to the Si NWs. The substrates were then used without a washing step.

Confluent human fibroblasts, previously differentiated from embryonic stem cells, were removed from culture flasks by a five minute trypsin treatment. After quenching the enzyme with culture media, the cells were re-suspended to a concentration of 1 million cells/mL. Next, 10 µL of the cell suspension was plated atop the sample and they were placed in the incubator (5% $CO_2$, 90% relative humidity). After 15 minutes of incubator, 700 µL of additional media was added.

After 18 hours of additional incubation, the samples were imaged. Subsequently, the cells were removed from the underlying substrate by treating the samples with trypsin for 10 minutes. Thereupon, the cells were replated on 8 mm glass coverslips and placed back into the incubator. After 3 hours, the settled cells were imaged in epifluorescence (Hg lamp) on an Olympus upright microscope. Unexpectedly, more than 95% of the cells fluoresced, indicating a successful delivery of the peptide with high efficiency (>95%).

Example 4

Antibody Delivery

Delivery of antibodies using the silicon substrates with vertically etched Si NWs prepared in Example 1 was tested in a manner similar to that described in Example 3.

A 1 µM solution of Qdot® 585 goat F(ab')2 anti-Rabbit IgG conjugate (H+L) solution was deposited on the surface of the silanized substrates so that the antibody was electrostatically bound to the Si NWs. The substrates were then used without a washing step.

Confluent human fibroblasts, previously differentiated from embryonic stem cells, were removed from culture flasks by a five minute trypsin treatment. After quenching the enzyme with culture media, the cells were re-suspended to a concentration of 1 million cells/mL. Next, 10 µL of the cell suspension was plated atop the sample and they were placed in the incubator (5% $CO_2$, 90% relative humidity). After 15 minutes of incubator, 700 µL of additional media was added.

After 18 hours of additional incubation, the samples were imaged. Subsequently, the cells were removed from the underlying substrate by treating the samples with trypsin for 10 minutes. Thereupon, the cells were replated on 8 mm glass coverslips and placed back into the incubator. After 3 hours, the settled cells were imaged in epifluorescence (Hg lamp) on an Olympus upright microscope. Unexpectedly, more than 95% of the cells fluoresced, indicating delivery efficiency higher than 95%.

Example 5

Protein Delivery

Delivery of proteins using the silicon substrates with vertically etched Si NWs prepared in Example 1 was tested in a manner similar to that described in Example 3.

A 1 mg/mL solution of recombinant green fluorescent protein (Evrogen TurboGFP) was deposited on the surface of the silanized substrates so that the protein was electrostatically bound to the Si NWs. The substrates were then used without a washing step.

Confluent human fibroblasts, previously differentiated from embryonic stem cells, were removed from culture flasks by a five minute trypsin treatment. After quenching the enzyme with culture media, the cells were re-suspended to a concentration of 1 million cells/mL. Next, 10 µL of the cell suspension was plated atop the sample and they were placed in the incubator (5% $CO_2$, 90% relative humidity). After 15 minutes of incubator, 700 µL of additional media was added.

After 18 hours of additional incubation, the samples were imaged. Subsequently, the cells were removed from the underlying substrate by treating the samples with trypsin for 10 minutes. Thereupon, the cells were replated on 8 mm glass coverslips and placed back into the incubator. After 3 hours, the settled cells were imaged in epifluorescence (Hg lamp) on an Olympus upright microscope. Unexpectedly, more than 90% of the cells fluoresced, indicating delivery efficiency higher than 90%.

Example 6

Nucleic Acid Delivery

Delivery of nucleic acids using the silicon substrates with vertically etched Si NWs prepared in Example 1 was tested in a manner similar to that described in Example 3.

A 1 mg/mL solution of an Alexa 488 labeled oligonucleotide in tris-buffered saline was deposited on the surface of the silanized substrates so that the oligonucleotide was electrostatically bound to the Si NWs. The substrates were then used without a washing step.

Confluent human fibroblasts, previously differentiated from embryonic stem cells, were removed from culture flasks by a five minute trypsin treatment. After quenching the enzyme with culture media, the cells were re-suspended to a concentration of 1 million cells/mL. Next, 10 µL of the cell suspension was plated atop the sample and they were placed in the incubator (5% $CO_2$, 90% relative humidity). After 15 minutes of incubator, 700 µL of additional media was added.

After 18 hours of additional incubation, the samples were imaged. Subsequently, the cells were removed from the underlying substrate by treating the samples with trypsin for 10 minutes. Thereupon, the cells were replated on 8 mm glass coverslips and placed back into the incubator. After 3 hours, the settled cells were imaged in epifluorescence (Hg lamp) on an Olympus upright microscope. Unexpectedly, more than 95% of the cells fluoresced, indicating delivery efficiency higher than 95%.

Example 7

Control Over Cellular Growth and Differentiation

Si NWs were grown on a Si substrate via CVD. Substrates were first prepared by immobilizing Au nanoparticles on a precleaned Si (111) substrate using a thin polyelectrolyte layer as previously described (*J. Am. Chem. Soc.* 2008, 130, 6252-6258; *Nano Lett.* 2004, 4, 1987-1990; *J. Am. Chem. Soc.* 2001, 123, 9769-9779; *J. Am. Chem. Soc.* 2008, 130, 6252-6258). Si NWs were then synthesized by the vapor transport method using $SiCl_4$ as the precursor for Si NW growth and $H_2$ (10%) in argon as the carrier gas with minor modifications from that which was previously reported (*Nano Lett.* 2005, 5, 457-460). Briefly, a Si (111) substrate, covered with Au nanoparticles patterned into stripes by flowing a solution of 70 nm Au nanoparticles across poly-l-lysine coated silicon using PDMS microfluidic channels, was placed inside a 1" diameter quartz tube and loaded at the center of a 12" horizontal tube furnace (Lindberg/Blue M). After the quartz tube was evacuated and flushed repeatedly with H$_2$ (10%) in argon gas mixture to minimize oxygen contamination, it was charged with H$_2$ (10%) in argon gas up to 760 torr and the pump line was quickly replaced with a line that enabled venting through a bubbler filled with a saturated K$_2$CO$_3$ aqueous solution, meant to trap the byproduct of SiCl$_4$ decomposition, gaseous HCl. The flow rate of H$_2$ (10%) in argon gas was adjusted down from 1000 sccm to 250 sccm, when the temperature of the furnace, heated at a rate of 16.6° C./min, reached 840° C., and the second stream of H$_2$ (10%) in argon gas, set at 50 sccm, was passed through the bubbler filled with SiCl$_4$ to carry the saturated SiCl$_4$ vapor into the reaction zone. After a 10 min reaction, the valves of the bubbler were closed and 300 sccm of Ar gas was purged through the quartz tube to quickly cool it down. The resulting Si substrates were examined under SEM for vertical Si NW growth and then cut into pieces of ~2 mm×5 mm for subsequent usage.

The Si NWs were then silanized by the method described in Example 3. The silanized Si NWs were then coated with a small amount of aqueous solution (5 uL) of Basal Medium Eagle (BME) containing Ara-C (i.e., Cytarabine, an anti-mitotic agent, at a concentration of 1 mg/mL). Once the water in the solution had evaporated, passaged neurospheres, neural precursor cells (NPCs) (*Nature Protocols*, 2008, 3, 935-940), were plated on the substrates as small drops so as to yield a final density of ~5×10$^4$ cells/cm$^2$. After incubation for 15 min, a BME/FBS based media was added (*J. Neurosci. Methods*, 2004, 136, 151-163). One day later, each sample was gently washed in PBS and transferred into fresh media. An additional feeding (a 50% media swap) was performed on the fourth day. On the sixth day, the cells were removed from the incubator, washed in PBS, and then examined. Subsequently, a standard immunofluorescence protocol was followed. The samples were fixed in 4% formaldehyde for 1 hour, permeablized for 15 minutes using a 1% triton-x 100 solution, and blocked using a 10% goat serum in PBS. After washing with PBS, primary antibodies against the relevant sub-cellular structures (i.e., chicken anti-neurofilament h antibody against neuron and rabbit anti-gfap antibody against glia) were added (at about a 1:500 dilution, obtained from Chemicon) and the samples were shaken overnight at 4° C. The following day, after washing with PBS, fluorescently labeled secondary antibodies were added. The samples were then shaken for 1 hour at room temperature, washed three times with PBS, and images were taken with an upright microscope (Olympus) and a mercury lamp (EXFO X-Cite).

It was observed that while NPCs differentiated into both mitotic (glial) and non-mitotic (neuronal) cell types. In regions containing NWs, the mixture was neuron heavy; in regions without NWs, only mitotic cell types were observed. While the mitotic cells (glial) grew to fill-in the regions containing no NWs, it was observed that when a glial-like cell was plated atop a set of Ara-C coated NWs, it survived but did not proliferate.

Example 8

Control Over Cellular Function

Apoptosis Induction:
The silanized Si NWs (produced via CVD prior to silanization) were treated with 100 mM Ac-DEVD-CHO, an apoptosis inhibitor, in PBS at room temperature for 1 hr, and washed in PBS three times for 2 min each. HeLa cells (5×10$^4$ cells/mL) in DMEM media were added onto the Si NWs, and cultured in a CO$_2$ incubator at 37° C. overnight. The cell treated Si NWs were then transferred into a fresh DMEM media containing actinomycin-D at the final concentration of 1 µg/mL, and incubated in a CO$_2$ incubator at 37° C. for 30 min, followed by addition of TNF-α at the final concentration of 2 ng/mL. After incubation in CO$_2$ incubator at 37° C. for indicated hours, the cells on the Si NWs were assayed for apoptosis.

Apoptosis Assay:
Cells were analyzed for apoptosis by the Terminal Deoxynucleotide Transferase dUTP Nick End Labeling (TUNEL) assay or by the Annexin V assay. TUNEL staining was performed using the apoptosis detection kit according to the manufacturer's protocol with minor modifications. Briefly, the cells on the Si NWs treated with actinomycin-D and TNF-α were washed in PBS three times for 2 min each. After fixation with 4% paraformaldehyde in PBS for 15 min and washes in PBS three times for 5 min each, the cell-containing Si NWs were incubated in PBS containing 0.5% Tween-20 and 0.2% BSA for 15 min at room temperature and washed in PBS for 2 min. Freshly prepared TdT end-labeling cocktail by mixing TdT buffer, biotin-dUTP and TdT at a ratio of 90:5:5, respectively, was then added to the cell-containing Si NWs, which was incubated for 1 hr at room temperature. The reaction was stopped by removing the TdT end-labeling cocktail and immersing the Si NWs in TB buffer for 5 min at room temperature, followed by washing in PBS four times for 2 min. The blocking buffer was then applied to the Si NWs, which were further incubated for 20 min at room temperature. After blocking, streptavidin-Cy3 at 20 µg/mL and WGA Alexa Fluor 488 at 50 µg/mL were incubated with the Si NWs for 30 min at room temperature, and washed in PBC three times for 5 min each, followed by examination under a fluorescence microscope. For Annexin V staining, the cells on the Si NWs treated with actinomycin-D and TNF-α and washed in PBS and binding buffer (10 mM HEPES, 140 mM NaCl, 2.5 mM CaCl$_2$, pH 7.4) were treated with Annexin V-FITC at the final concentration of 1 µg/mL. After incubation for 15 min at room temperature and washes in binding buffer three times for 1 min each, cells were analyzed under a fluorescence microscope.

It was found that the cells in contact with the Si NWs coated with Ac-DEVD-CHO survived while the cells in contact with the Si NWs not coated with the inhibitor died. This observation indicates that Ac-DEVD-CHO was successfully delivered into the cells.

Example 9 siRNA Delivery

Two anti-Vimentin siRNA solutions were prepared in water: the first one consisted of Alexa Fluor 546 labeled Hs_VIM_11 HP Validated siRNA (sense strand: 5'-GAUC-CUGCUGGCCGAGCUCtt-Alexa Fluor 546-3'; SEQ ID NO: 1); and the second one consisted of equal parts of Hs_VIM_11 HP Validated siRNA, Hs_VIM_4 HP Validated siRNA (sense strand: 5'-GGCACGUCUUGACCUUGAAtt-Alexa Fluor 546-3'; SEQ ID NO: 2), and Hs_VIM_5 HP Validated siRNA (5'-GAAGAAUGGUACAAAUCCAtt-Alexa Fluor 546-3'; SEQ ID NO: 3). As a control, Alexa Fluor 546 and Alexa Fluor 647 labeled AllStar Negative siRNAs were used. All above-mentioned siRNAs were obtained from Qiagen. For sodium channel knockdown experiments, custom siRNAs were ordered from Qiagen. The 21-mers used were made by targeting against 19-mer sense sequences chosen from prior shRNA experiments described in Xu et al, *J Neurosci Res* 2005, 79(4): 428-41. Na$_V$1.X targeted siRNA sense strand has a sequence of 5'-UCGACCCUGACGC- CACUtt-Alexa Fluor 546-3' (SEQ ID NO: 4) and GNU targeted siRNA sense stand has a sequence of 5'-ACUGAGAACUAAGAGAGtt-Alexa Fluor 546-3' (SEQ ID NO: 5).

HeLa S3 cells were plated on anti-Vimentin siRNA-coated Si NWs in a manner similar to that described in Example 3. At day two, a full media swap was performed. Subsequently, a standard immunofluorescence protocol was followed. The samples were fixed in 4% formaldehyde in PBS for 20 min at room temperature, permeablized using a 0.25% triton-x 100 in PBS (RT, 10 minutes), and blocked using a 10% goat serum in PBS (RT, 1 hour). After washing with PBS, primary antibodies against the relevant sub-cellular structures (i.e., mouse anti-vimentin) were added to 5% goat serum in PBS at 1:250 dilution and the samples were shaken overnight at 4° C. The samples were then washed with PBS and incubated with Alexa Fluor labeled secondary antibodies (1:500 dilution) in 2.5% goat serum in PBS (RT, 1 hour). For more details, see Proc. Natl. Acad. Sci. 2010, 107, 1870-1875. After washing with PBS, the immunostained cells were visualized using both epifluorescence and confocal imaging (Olympus). Confocal laser powers and gains were set using HeLa cells receiving control AllStar Negative siRNA and three-dimensional image reconstructions were made using BitPlane (Imaris). Substantial knockdown was seen when the Si NWs were used to deliver individual or pooled siRNAs against vimentin; no knockdown was seen when either a control siRNA or no molecule was used. As a control, a conventional siRNA delivery reagent, Hyperfect (Qiagen), was used according to the manufacturer's recommendations. Results obtained from either NW-based or Hyperfect-based delivery were similar as determined by immunofluorescence and Q-PCR.

Sodium channel knockdowns were performed by plating E18 rat hippocampal neurons on siRNA-coated, grown Si NWs as above. Electrophysiological measurements were made at day eight after plating. It was found that neurons transfected with $Na_v1.X$ channel-targeting siRNAs exhibited substantially reduced sodium currents in response to depolarizing voltage steps. In contrast, GNU-transfected cells showed normal inward sodium currents. Following patch clamp recordings, samples were fixed, immunostained (as above), and analyzed. Immunostaining for the alpha subunit of $Na_v1.1$ confirmed that substantial knockdown had been achieved. Similar results were obtained using plasmids that coexpressed EGFP and short hairpin RNAs directed at the $Na_v1.X$ transcripts. This observation indicates that siRNAs were successfully delivered into the cells.

Example 10

Microarray Patterning

Site-specific, biologically effective molecule delivery was achieved by printing different molecules (e.g., siRNA, purified recombinant proteins, and labeled IgGs) on Si NW substrates using a Nanoprint contact array printer (Arrayit). The printer was equipped with a flathead, square pin (NS6) of 150 µm width. Single depositions of samples were printed as an array at a pitch of 300 to 500 µm using samples ranging in concentrations from 200 to 400 µM. For arrays containing multiple sample types, the second sample was printed offset from the first after the first was fully arrayed.

More specifically, a 400 µm pitch checkerboard pattern of Alexa Fluor 488 labeled histone H1 and Alexa Fluor 546 labeled siRNA targeting the intermediate filament vimentin was printed onto Si NW surfaces. The Si NW surfaces were then seeded with HeLa S3 cells. The cells were immunostained in a manner similar to that described in Example 9 and were then imaged using fluorescence microscopy. Substantial knockdown of vimentin was observed in the majority of HeLa S3 cells sitting atop the siRNA sites. Meanwhile, the labeled histones were delivered and actively transported to the nuclei of the HeLa S3 cells sitting atop the histone microarray spots. Similar results were obtained using a variety of other targeted proteins and peptides.

Example 11

Molecular Delivery to Human B Cells

Normal and cancerous human B cells (obtained directly from two cancer patients) were plated on different Si NW substrates (NW length: 2000-4000 nm; diameter: 150-200 nm; NW density: 0.1-5 wire/µm$^2$) in a manner similar to that described in Example 2.

The cells were examined 2 days after plating. Membranes were labeled with fluorescein diacetate (green) and dead nuclei were counterstained with propidium iodide (magenta). Live cells were green sans magenta nuclei and dead cells were green with magenta nuclei. Unexpectedly, normal human B cells had a survival rate of at least 60% and the cancerous B cells had a survival rate of 95-100%.

Fluorescent biomolecules, i.e., Cy3-labeled plasmid DNAs or Cy3-labeled siRNAs, were delivered to the normal and cancerous cells by plating those cells on top of NWs coated with those fluorescent biomolecules in a manner similar to that described in Example 3. The cells were then imaged after two days using a confocal microscope, in a manner similar to that described in Example 9. Unexpectedly, more than 90% of the normal cells and cancerous cells plated on siRNA-coated NWs fluoresced, indicating delivery efficiency higher than 90%. Delivery efficiency of plasmid DNA to normal B cells was higher than 90% while that to the cancerous cells was between 50-75%.

Example 12

Molecular Delivery to Dendritic Cells

Dendritic cells were plated on flat Si or different Si NW substrates (NW length: 1000-1500 nm; diameter: 150-200 nm; NW density: 0.1-5 wire/µm$^2$) in a manner similar to that described in Example 2. Si NWs alone did not induce immune responses from dendritic cells. Nor did they prevent normal responses when those cells were stimulated with pathogens.

Delivery of molecules (including small molecules, plasmid DNA, siRNA, phiYFP-peroxisome protein) to dendritic cells on top of NWs was carried out in a manner similar to that described in Example 3. Si NWs, when used to deliver molecules, did not induce immune responses from dendritic cells. Nor did they prevent responses from those cells when they were stimulated with pathogens.

Example 13

Molecular Delivery to Stem Cells

Si NWs were used to study the ability of different molecules to influence cell fate.

Induced pluripotent stem cells (iPS cells) were plated on different Si NW substrates (NW length: 2000-4000 nm; diameter: 150-200 nm; NW density: 0.1-5 wire/$\mu m^2$) in a manner similar to that described in Example 2. It was found that iPS cells plated on Si NWs not only maintained pluripotency but also divided into iPS cells with pluripotency.

Delivery of molecules (including plasmid DNA and siRNA) to iPS cells on top of NWs was carried out in a manner similar to that described in Example 3. It was found that the molecules were delivered to the cells without affecting the cells' pluripotency.

Mouse embryonic stem cells (mES cells) were also used in this study. Delivery of molecules (including Cre Recombinase proteins) into mES cells was carried out in a manner similar to that described in Example 3. It was found that the molecules were efficiently delivered to the cells without affecting the cells' pluripotency. Also, it was observed that transgenic foxed-eGFP mES cells expressed EGFP resulting from the delivery of Cre Recombinase proteins by Si NWs.

Other Embodiments

All of the features disclosed in this specification may be combined in any combination. Each feature disclosed in this specification may be replaced by an alternative feature serving the same, equivalent, or similar purpose. For example, two or more linkers can be applied to connect the molecule to be delivered to the nanowires. As in another example, the molecule to be delivered are connected to the nanowires without a linker.

Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A system comprising:
a substrate having a surface;
a plurality of nanowires attached to the surface;
a plurality of cells of a first cell type or a second cell type penetrated by at least one nanowire of the plurality of nanowires; and
a plurality of molecules to be delivered to the plurality of cells,
wherein at least one of the nanowires further comprises a surface layer of a silicon-containing material, a first silane linker covalently bound thereto, and a first molecule of the plurality of molecules electrostatically bound to the first silane linker,
wherein at least one cell of the plurality of cells penetrated by the at least one nanowire of the plurality of nanowires further contains at least some of the first molecule within the cytoplasm and not electrostatically bound to the first silane linker,
wherein the plurality of nanowires has a diameter of less than 200 nm, a length of 2.5-5 μm, and a density of 0.5-5 nanowires/μm$^2$ configured for high delivery efficiency to the first cell type or a diameter of less than 200 nm, a length of 0.5-2.5 μm, and a density of 0.01-10 nanowires/μm$^2$ configured for high delivery efficiency to the second cell type,
wherein the first cell type is different from the second cell type, and
wherein a second molecule of the plurality of molecules is attached to a second silane linker, the second molecule being different from the first molecule, wherein the first molecule and the second molecule are connected to the same nanowire via the respective silane linkers.

2. The system of claim 1, wherein the nanowires are attached to the surface along a substantially vertical direction relative to the surface.

3. The system of claim 1, wherein the first molecule is reversibly and electrostatically bound to the first silane linker.

4. The system of claim 1, wherein the first molecule is a protein, a polysaccharide, or a small molecule.

5. The system of claim 1, wherein the second molecule is a nucleic acid, a protein, a polysaccharide, or a small molecule.

6. The system of claim 1, wherein the silicon-containing material is silicon oxide, silicon nitride, or silicon carbide.

7. The system of claim 1, wherein the first silane linker is propylaminosilane.

8. The system of claim 1, wherein the first silane linker is (3-aminopropyl)-trimethoxysilane, (11-aminoundecyl)-triethoxysilane, (3-mercaptopropyl)-trimethoxysilane, or (11-mercaptoundecyl)-trimethoxysilane.

9. The system of claim 1, wherein the plurality of cells comprises a primary cell, an immune cell, a neuron, a fibroblast, or a stem cell.

10. The system of claim 1, wherein the first molecule is RNA.

11. The system of claim 1, wherein at least 50% of the plurality of cells are penetrated by at least one nanowire of the plurality of nanowires and further contain at least some of at least one molecules of the plurality of molecules within the cytoplasm and not electrostatically bound to the silane linkers.

12. A system comprising:
a microarray substrate comprising a plurality of nanowires and a plurality of molecules deliverable to a plurality of cells of a first cell type or a second cell type, wherein the molecules deliverable to the plurality of cells are electrostatically bound to silane linkers covalently bound to the plurality of nanowires such that upon insertion of the nanowires into the cells, at least one molecule of the plurality of molecules deliverable to the plurality of cells is released from at least one of the silane linkers into the cytoplasm of at least one cell of the plurality of cells,
wherein the plurality of nanowires has a diameter of less than 200 nm, a length of 2.5-5 μm, and a density of 0.5-5 nanowires/μm$^2$ configured for high delivery efficiency to the first cell type or a diameter of less than 200 nm, a length of 0.5-2.5 μm, and a density of 0.01-10 nanowires/μm$^2$ configured for high delivery efficiency to the second cell type,
wherein the first cell type is different from the second cell type, and
wherein the plurality of molecules further comprises a second molecule, the second molecule being different from the at least one molecule, wherein the second molecule is attached to a second silane linker, wherein the at least one molecule and the second molecule are connected to the same nanowire via the respective silane linkers.

13. The system of claim 12, wherein the plurality of nanowires are attached to the substrate along a substantially vertical direction relative to the substrate.

14. The system of claim 12, wherein the plurality of molecules deliverable to the plurality of cells comprise a protein, a polysaccharide, or a small molecule.

15. The system of claim 12, wherein the plurality of molecules deliverable to the plurality of cells comprise RNA.

16. The system of claim 12, wherein the silane linkers are covalently bound to a silicon-containing material on the surfaces of the plurality of nanowires, wherein the silicon-containing material comprises silicon oxide, silicon nitride, or silicon carbide.

17. The system of claim 12, wherein the silane linkers comprise propylaminosilane, (3-aminopropyl)-trimethoxysilane, (11-aminoundecyl)-triethoxysilane, (3-mercaptopropyl)-trimethoxysilane, or (11-mercaptoundecyl)-trimethoxysilane.

18. A method, comprising:
providing a substrate having a surface, a plurality of nanowires attached to the surface, and a plurality of molecules, wherein at least one of the nanowires further comprises a surface layer of a silicon-containing material, a first silane linker and a second silane linker covalently bound thereto, and a first molecule and a second molecule of the plurality of molecules, wherein the first molecule is electrostatically bound to the first silane linker and the second molecule is electrostatically bound to the second silane linker, wherein the plurality of nanowires has a diameter of less than 200 nm, a length of 2.5-5 μm, and a density of 0.5-5 nanowires/μm$^2$ configured for high delivery efficiency to a first cell type or a diameter of less than 200 nm, a length of 0.5-2.5 μm, and a density of 0.01-10 nanowires/μm$^2$ configured for high delivery efficiency to a second cell type; and contacting the plurality of nanowires with a plurality of cells of the first cell type or the second cell type to allow penetration of at least a portion of the nanowires into at least some of the cells, wherein at least one cell of the plurality of cells contains at least the first molecule of the plurality of molecules.

* * * * *